United States Patent
Wang et al.

(10) Patent No.: US 10,094,814 B2
(45) Date of Patent: Oct. 9, 2018

(54) PERFORMANCE TESTING DEVICE FOR ACID FRACTURING FLUID AND APPLICATION THEREOF

(71) Applicant: PetroChina Company Limited, Dongcheng District, Beijing (CN)

(72) Inventors: Haiyan Wang, Langfang (CN); Yongjun Lu, Langfang (CN); Baoshan Guan, Langfang (CN); Xiaohui Qiu, Langfang (CN); Hua Ming, Langfang (CN); Ping Liu, Langfang (CN); Wen Zhai, Langfang (CN)

(73) Assignee: PetroChina Company Limited, Beijing (CN)

( * ) Notice: Subject to any disclaimer, the term of this patent is extended or adjusted under 35 U.S.C. 154(b) by 292 days.

(21) Appl. No.: 15/201,654

(22) Filed: Jul. 5, 2016

(65) Prior Publication Data

US 2017/0009576 A1 Jan. 12, 2017

(30) Foreign Application Priority Data

Jul. 7, 2015 (CN) .......................... 2015 1 0395271

(51) Int. Cl.
*E21B 49/00* (2006.01)
*G01N 33/24* (2006.01)
(Continued)

(52) U.S. Cl.
CPC ............... *G01N 33/24* (2013.01); *C09K 8/72* (2013.01); *G01N 11/00* (2013.01)

(58) Field of Classification Search
CPC .................................................... G01M 17/027
(Continued)

(56) References Cited

U.S. PATENT DOCUMENTS 4,572,009 A 2/1986 Brauer et al.

FOREIGN PATENT DOCUMENTS

CN 201218811 Y * 4/2009
CN 102174883 A 9/2011
(Continued)

OTHER PUBLICATIONS

First Office Action and Search Report issued in corresponding Chinese Patent Application No. 201510395271.6 dated Mar. 29, 2017, along with the English translation.
(Continued)

*Primary Examiner* — John Fitzgerald
*Assistant Examiner* — Rodney T Frank
(74) *Attorney, Agent, or Firm* — Renner, Otto, Boisselle & Sklar, LLP (57) ABSTRACT

A performance testing device for acid fracturing fluid includes: two semiterete rock core holders, the flat face sides of the two semiterete rock core holders being arranged opposite to each other; the two semicircle sides of the two semiterete rock core holders being provided with a rotation member which is opened with a first groove; the two semiterete rock core holders being able to rotate about a first rotation axis formed corporately by the two rotation members; a pressure applying shell having a recessed portion that matches with the curved face side, the recessed portion being able to cooperate with the curved face side, the pressure applying shell being able to apply a pressure to the two rock core holders to bring the two flat face sides thereof together.

13 Claims, 7 Drawing Sheets

(51) Int. Cl.
   *G01N 11/00* (2006.01)
   *C09K 8/72* (2006.01)
(58) Field of Classification Search
   USPC .......................................................... 73/146
   See application file for complete search history.

(56) References Cited

FOREIGN PATENT DOCUMENTS

| CN | 103244112 A | 8/2013 |
| CN | 104407103 A | 3/2015 |
| CN | 104594886 A | 5/2015 |
| CN | 204807417 U | 11/2015 |

OTHER PUBLICATIONS

Beg et al., "A System Experimental Study of Acid Fracture Conductivity", Foreign Oilfield Engineering, vol. 17, No. 2, Feb. 2001, along with English version published in Nov. 1998.

\* cited by examiner

PERFORMANCE TESTING DEVICE FOR ACID FRACTURING FLUID AND APPLICATION THEREOF

This application claims priority of Chinese Application No. 201510395271.6 filed Jul. 7, 2015, which is hereby incorporated herein by reference.

TECHNICAL FIELD

This invention pertains to the field of performance test for acid fracturing fluid, particularly relating to a performance testing device for acid fracturing fluid and application thereof.

BACKGROUND TECHNOLOGY

Acid fracturing refers to squeeze acid fluid into wells under a pressure higher than the pressure of cracks or closing to the pressure of natural fractures so as to form fractures in reservoirs, while the acid fluid reacts with rocks in the fractures and unevenly etches the rocks in the fractures. A formed groove-shaped or unevenly etched fracture is incompletely closed after the construction is finished, and finally forms an artificial fracture that has a certain physical dimension and flow conductivity, which can improve the flow conducting situation of an oil and gas well, and thereby increase the production of the oil and gas well.

In general, a method of testing the flow conductivity of acid fracturing fluid in laboratory is to place two rock cores in parallel, and applies a closing pressure to the two rock cores which can bring them together, and then forces the acid fracturing fluid to enter the two rock cores to perform acidic etching. The problem thereof is that the angle of the fracture for simulating the stratum is less diversified, and cannot achieve actual simulation of the practical situation, and leads to the result of the test to be not accurate enough.

SUMMARY

The purpose of this application is to provide a performance testing device for acid fracturing fluid to improve accuracy of the test for the flow conductivity of the acid fracturing fluid.

In order to solve the above technical problem, the embodiments of this application provide a performance testing device for acid fracturing fluid, which is implemented as follows:

A performance testing device for acid fracturing fluid, comprising:
  two semiterete rock core holders have a curved face side, a flat face side and two opposite semicircle sides, the flat face side of the two semiterete rock core holders being arranged opposite to each other and being able to fix a rock core to be tested; the two semicircle sides of the holders being provided with a rotation member which is opened with a first groove; when the flat face sides of the holders are spaced apart at a predefined distance, the two rotation members are able to cooperate to form a first rotation axis, and the two first grooves are able to cooperate to form a first through hole; the two semiterete rock core holders are able to rotate about the first rotation axis, and the first through hole are able to be in communication with a gap formed between the rock cores fixed by the flat face sides of the holders;

a pressure applying shell having a recessed portion that matches with the curved face side of the—holder, the recessed portion are able to rotatably cooperate with the curved face side, the pressure applying shell are able to apply a pressure to the holders to make the two flat face sides thereof joint in a manner of surface contact.

According to the above device, the flat face side is opened with a slot in an axial direction of the holder, the slot is able to lock the rock core to be tested.

According to the above device, one of the recessed portion of the pressure applying shell and the curved face side of the holder is provided with a predefined number of blind holes in which balls are inlaid.

According to the above device, the predefined number of balls are divided into a predefined number of rows along an axial direction of the semiterete rock core holder to be inlaid in the blind holes;
  correspondingly, the other one of the recessed portion of the pressure applying shell and the curved face side of the rock core holder is provided with a predefined number of roll-grooves in a rotatable circumferential direction of the semiterete rock core holder, where in each of the roll-grooves corresponds to the ball in the same row.

The application further provides a system having the performance testing device for acid fracturing fluid according to any one of claims 1 to 4, comprising:
  a predefined number of the performance testing devices for acid fracturing fluid;
  a gripping device for gripping the performance testing devices for acid fracturing fluid; and
  a second rotation axis provided on the gripping device.

According to the above system, the gripping device comprises:
  a first support member for placing the performance testing devices for acid fracturing fluid;
  a second support member provided opposite to the first support member; and
  a connecting member that connects the first support member and the second support member, the second rotation axis being provided on the connecting member.

According to the above system, a first support column is provided between the first support member and the second support member, the first support column is opened with a predefined number of first axle holes, which have a predefined length in a direction determined by pointing from the first support member to the second support member;
  the first rotation axis is able to be placed in the first axle hole.

According to the above system, a pressure applying device is provided on the first support member and/or the second support member, the pressure applying device has an extendable pressure output shaft, and the pressure output shaft is able to be connected in a manner of abutting contact to the pressure applying shell.

According to the above system, the first support member and/or the second support member is able to be movably connected with the connecting member, and the movable direction is in accordance with a length direction of the first axle hole;
  one of the first support member and the second support member is fixedly connected with an end of the first support column;
  correspondingly, the other one of the first support member and the second support member is opened with a second through hole through which the other end of the first support column is able to pass movably;

a bolt is connected between the first support member and the second support member.

According to the above system, further comprising:
a second support column on which a second axle hole is provided;
the second rotation axis is able to be set in the second axle hole.

By means of the above technical solution, the advantageous effect of this invention lies in that: the performance testing device for acid fracturing fluid provided in this application prepares a rock core to be tested into semiterete, and a complete cylinder can be formed by arranging the flat face ends of two semiterete rock cores opposite to each other; the rotation member provided on the semicircle end face of each semiterete rock core can cooperate to form a rotation axis, and the pressure applying shell is set to have a recessed portion that can be matched to a curved face of the semiterete rock core; when the rock core rotates about the rotation axis, the recessed portion of the pressure applying shell can always apply a closing pressure to the rock cores through the curved face matched thereto, and during this process, changing measurements from various angles of the rock core can be realized without altering the pressure applying direction of the pressure applying shell.

BRIEF DESCRIPTION OF THE DRAWINGS

In order to explain more clearly the technical solution in the embodiments of this invention, the figures needed in the description of the embodiments will be briefly introduced in the following. Obviously, figures in the following description are only some embodiments of this invention, and for an ordinary person skilled in the art, other figures may also be obtained based on these figures without paying any creative effort.

DETAILED DESCRIPTION

Clear and comprehensive description of the technical solutions in the embodiments of this invention will be made in the following in combination with the figures in the embodiments of this invention. Obviously, the embodiments described herein are only part of the embodiments of the application rather than all the embodiments thereof. Based on the embodiments of this invention, all other embodiments obtained by the ordinary skilled persons in the field without paying any creative effort pertain to the extent of protection of this invention.

In the prior art, when testing the performance of acid fracturing fluid, a customary means is to fabricate a rock core to be tested into a flat plate shape, and applies a closing pressure to two flat plate-shaped rock cores which are arranged opposite to each other, and then introduces the acid fracturing fluid into a gap between the two flat plate-shaped rock cores to perform acidic etching. The problem thereof is that: since the flat plate-shaped rock cores are arranged opposite to each other, an orientation of the formed fracture is fixed, for example, the fracture is horizontal, and therefore this can simulate only one situation of horizontal fracture in the stratum. However, in practice, the trends of fractures in the stratum are various, such as horizontal fractures, vertical fractures and inclined fractures at any angles. Therefore, as regarding the acidic etching situation of the rock core by the acid fracturing fluid when simulating only the fracture at a single angle, the accuracy and value of reference of the test results are limited.

Besides, in the prior art, the direction of a pressure applied by the pressure applying shell is stable and unchanged, for example, a closing pressure is applied to the flat plate-shaped rock core by means of a pressure applying device such as that having a hydraulic rod or a pneumatic rod, and due to restrictions of its own device structure, the extending direction of the hydraulic rod or the pneumatic rod is unidimensional. Therefore, even if the two flat plate-shaped rock cores rotate, the direction of the pressure applied by the pressure applying shell will hardly be changed adaptively, resulting in that the multi-angle performance test for the acid fracturing fluid become difficult.

In view of the deficiency of the prior art that the single-angle test performed to the performance of the acid fracturing fluid leads to limited accuracy and value of reference of the test results, and that there are technical barriers in the prior art for realizing the performance test for the acid fracturing fluid at multiple angles, the embodiments of this application provide a performance testing device 10 for acid fracturing fluid which can well solve the above problem.

Figure 1:
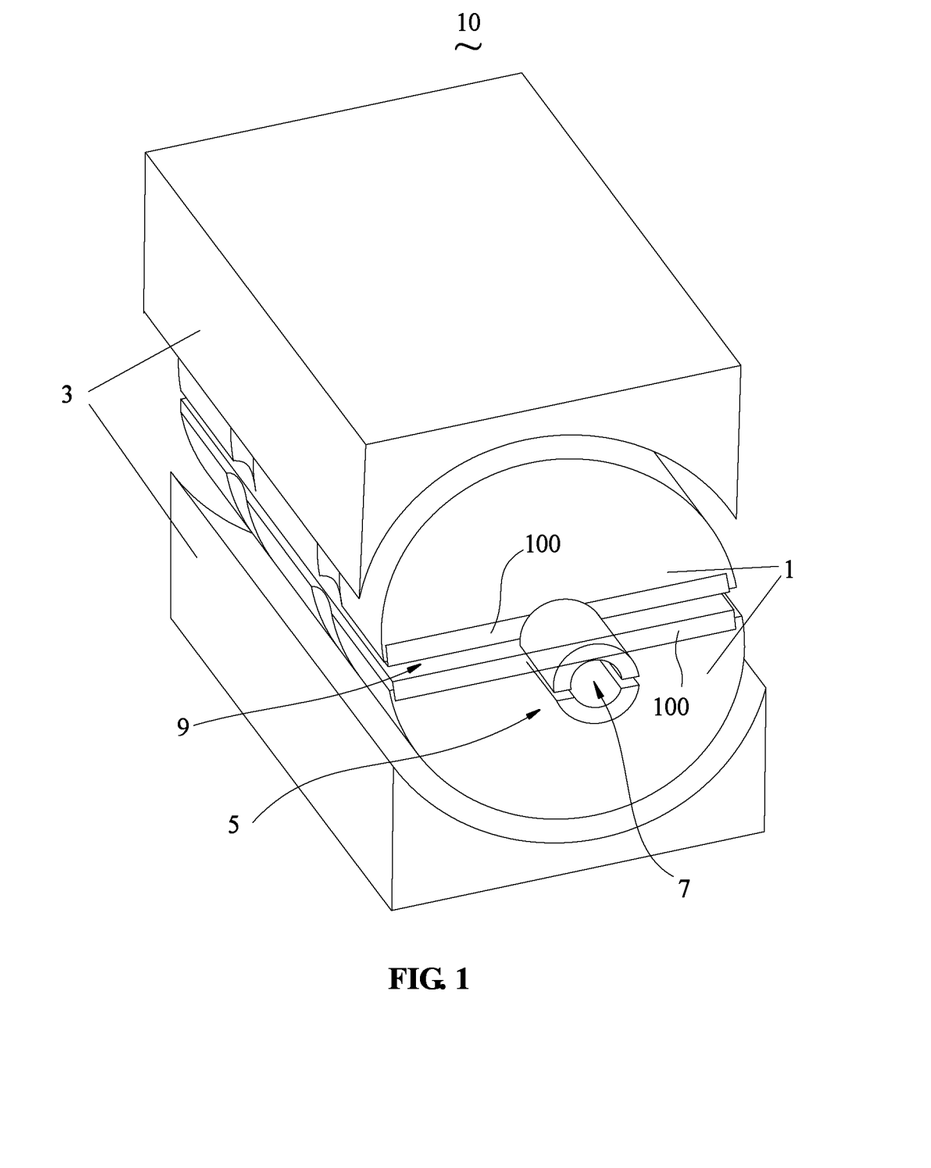
FIG. 1 is a structural diagram of the performance testing device for acid fracturing fluid of an embodiments of this invention.
Figure 2:
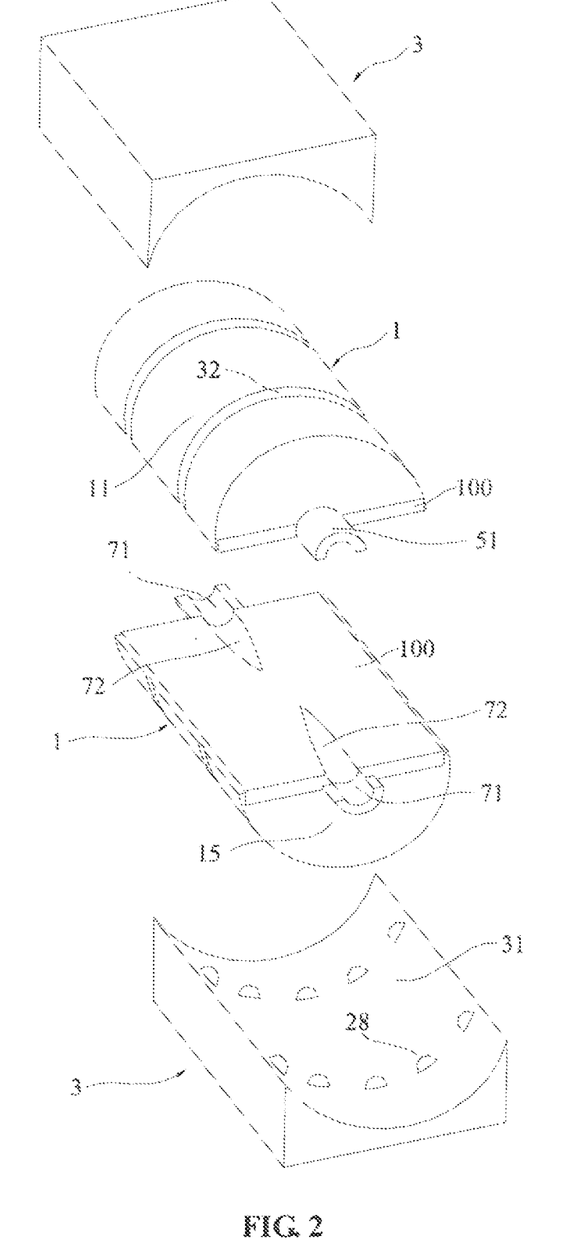
FIG. 2 is an explosion diagram of the performance testing device for acid fracturing fluid shown in FIG. 1.
Figure 3:
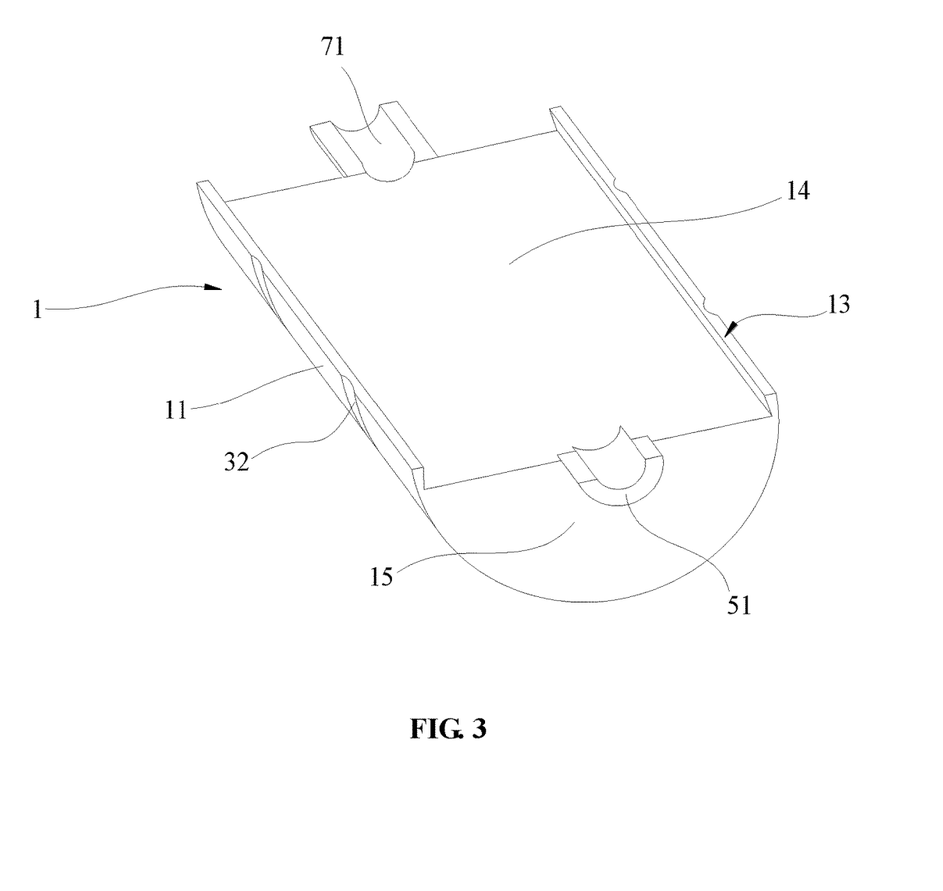
FIG. 3 is a structural diagram of the semiterete rock core holder.

Please refer to FIG. 1 to FIG. 3 together, the embodiments of this invention provide a performance testing device 10 for acid fracturing fluid, which comprises: two semiterete rock core holders 1 have a curved face side 11, a flat face side 13 and two opposite semicircle sides 15, the flat face side 13 of the two semiterete rock core holders are arranged opposite to each other and are able to fix a rock core 100 to be tested, the two semicircle sides 15 of the two semiterete rock core holders 1 are provided with a rotation member 51 which is opened with a first groove 71; when the flat face side 13 of the two semiterete rock core holders 1 are spaced apart at a predefined distance, the two rotation members 51 are able to cooperate to form a first rotation axis 5, and the two first grooves 71 are able to cooperate to form a first through hole 7, the two semiterete rock core holders 1 are able to rotate about the first rotation axis 5, the first through hole 7 are able to be in communication with a gap 9 formed between the rock cores 100 to be tested fixed by the flat face sides 13 of the two semiterete rock core holders 1; a pressure applying shell 3 have a recessed portion 31 which is matched to the curved face side 11 of the semiterete rock core holder 1, the recessed portion 31 are able to rotatably cooperate with the curved face side 11, and the pressure applying shell 3 are able to apply a pressure to the two semiterete rock core holders 1 to make the flat face sides thereof joint in a manner of surface contact.

The performance testing device for acid fracturing fluid of the embodiment of this application prepares a rock core to be tested into semiterete, and a complete cylinder is able to be formed by arranging the flat face sides of two semiterete rock cores opposite to each other; the rotation members provided on the semicircle sides of each semiterete rock core can cooperate to form a rotation axis, and the pressure applying shell is set to have a recessed portion that can be matched to the curved face of the semiterete rock core. When the rock core rotates about the rotation axis, the recessed portion of the pressure applying shell can always apply a closing pressure to the rock core through the curved face side matched thereto, and during this process, changing measurements of the rock core from multiple angles which can be realized without altering the pressure applying direction of applying shells.

In most situations, the maximum direction of a stratum stress is a direction which approximates horizontal direction, and the stratum stress in the vertical direction or in a direction of any other angle is smaller than the stress in the horizontal direction. Therefore, another advantageous effect of the embodiment in application is: when the semiterete rock core holder rotates, the pressure size applied by the pressure applying shell to the rock core also changes at the same time, and in particular, the value of the applied pressure decreases, and this is in accordance with the actual situation of the stratum stress.

Figure 4:
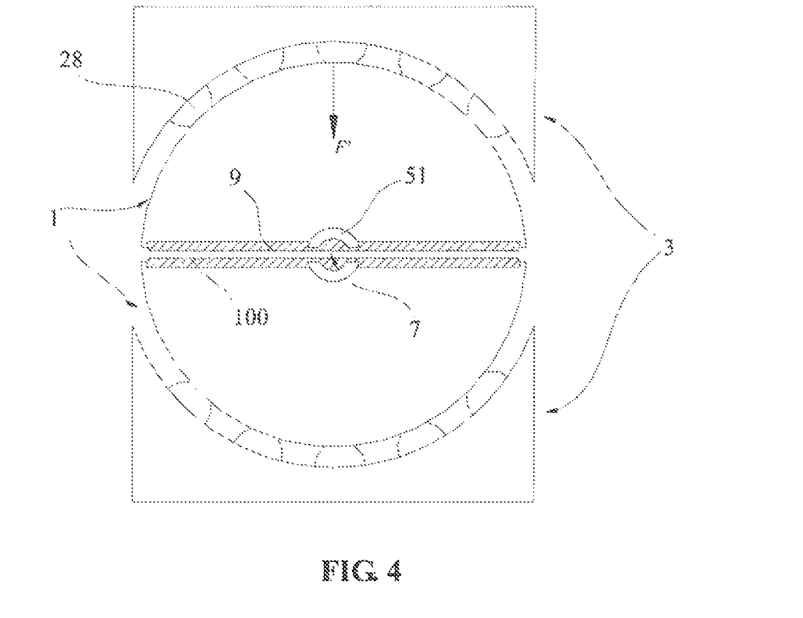
FIG. 4 is a side view of an embodiment of the performance testing device for acid fracturing fluid shown in FIG. 1.
Figure 5:
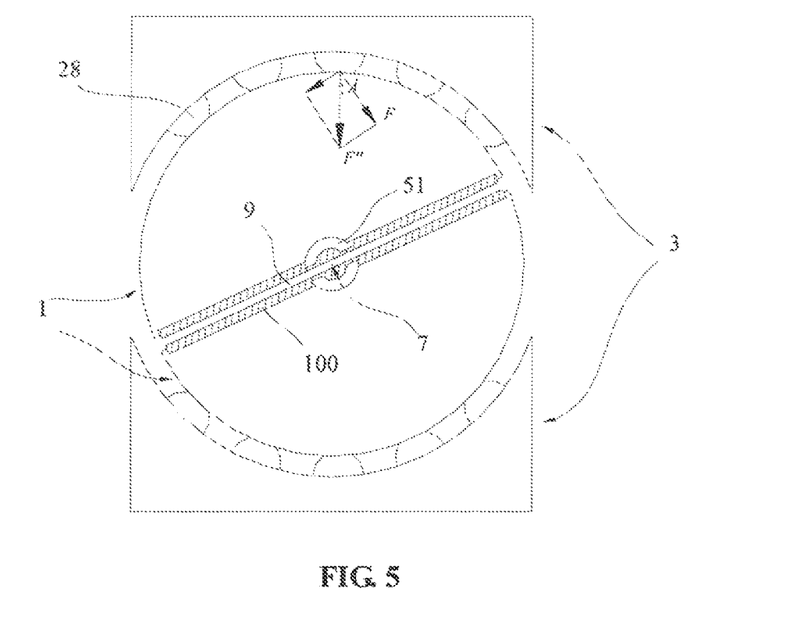
FIG. 5 is a side view of another embodiment of the performance testing device for acid fracturing fluid shown in FIG. 1.

In particular, please refer to FIG. 4 and FIG. 5. When the gap 9 formed between the rock core 100 to be tested fixedly provided by the flat face sides 13 of the two semiterete rock core holders 1 is horizontal, the pressure value applied by the pressure applying shell 3 to the rock core holders 1 through the curved face side 11 is F', at this time, the closing pressure applying on the rock core 100 to be tested is F=F'; when the two semiterete rock core holders 1 rotate for a certain angle $\alpha$, i.e., when the angle of the stratum fracture is $\alpha$, the pressure value applied by the pressure applying shell 3 to the rock core holders 1 through the curved face is F''', and at this time, the closing pressure acting on the rock core 100 is F=F'''·cos $\alpha$.

In a case where the pressure applied by the pressure applying shell 3 is fixed, an effective acting area between the recessed portion 31 of the pressure applying shell 3 and the curved face side 11 of the rock core holder 1 determines the size of the closing pressure acting on the rock cores 100 to be tested. As can be seen from FIGS. 4 and 5, when the gap 9 formed between the rock cores 100 to be tested is horizontal, the effective acting area between the recessed portion 31 of the pressure applying shell 3 and the curved face side 11 of the rock core holder 1 is maximum. In addition, when the rock core holder 1 rotates for a certain angle $\alpha$, a pressure applying shell 3 opposite to each rock core holder 1 will suffer an opposite force applied thereto by the other pressure applying shell 3. For example, as shown in FIG. 5, the pressure applying shell 3 located in a relatively lower place will apply an upward force to the rock core holder 1 located in a relatively upper place to thereby compensate a downward force applied to the rock core holder 1 by the pressure applying shell 3 which is matched thereto and located in a relatively upper place, and therefore the pressure applied by the corresponding pressure applying shell 3 to the rock core holder 1 is further decreased. In conclusion, F>F'≥F'''·cos $\alpha$, therefore, it is realized that the change of angles lead to the change of closing pressure, and thus the actual situation of the stratum stress is simulated authentically.

The embodiments of this application realizes causing of the change of the closing pressure by rotation of the rock core holder 1, in a case where the size of the pressure output by the pressure applying shell 3 is unchanged. Of course, a person skilled in the art should understand that the application in the embodiments is not limited to the scene that the maximum direction of stratum stress is a direction which approximates the horizontal direction. When the maximum direction of stratum stress is at any other angle, the size of pressure output by the pressure applying shell 3 is able to be altered to compensate the change of the angle and the influence of an effective acting area between the curved face side 11 of the rock core holder 1 and the recessed portion 31 of the pressure applying shell to the closing pressure.

There are many ways of fixing the rock core 100 to be tested on the flat face side 13, for example, the rock core 100 to be tested may be adhered and fixed to the flat face side 13, and clamp splices may be set on the two semicircle sides 15 to tightly clamp the rock core 100 to be tested, and the following method may also be used, which can be seen in FIG. 3. In some embodiments of this application, a slot 14 may be opened on the flat face side 13 in an axial direction of the semiterete rock core holder 1, and the rock core 100 to be tested is locked in the slot 14.

For ease of rotation, a lubricant may be applied on the curved face side 11 of the rock core holder 1 and the recessed portion 31 of the pressure applying shell 3 matched thereto, so as to reduce as far as possible rigid frictions between the two. And, in order to further reduce the friction between the curved face side 11 and the recessed portion 31, in some embodiments of this application, the two may also be changed from slide contact to rolling contact. In particular, please referring to FIGS. 2, 4 and 5. One of the recessed portion 31 of the pressure applying shell 3 and the curved face side 11 of the rock core holder 1 is provided with a predefined number of blind holes (not shown in the figures), and balls 28 are inlaid in the predefined number of blind holes. By the embodiment of this application, frictions between the two can be greatly reduced and the force for rotating the rock core holder 1 is decreased, and thus the rotation becomes easier.

In order to prevent the rock core holder 1 and the pressure applying shell 3 from fleeing in an axial direction, in some embodiments of this application, the predefined number of balls 28 are divided into a predefined number of rows along an axial direction of the semiterete rock core holder 1 to be inlaid in the blind holes, correspondingly, the other one of the recessed portion 31 of the pressure applies in shell 3 and the curved face side 11 of the rock core holder 1 is provided with a predefined number of roll-grooves 32 in a rotatable circumferential direction of the semiterete rock core holder 1, wherein each of the roll-grooves 32 corresponds to the ball 28 in the same row. As shown in FIG. 2, this is namely to inlay the balls 28 in the blind holes opened on the recessed portion 31 and to provide roll-grooves 32 on the curved face side 11. Of course, in practice, the balls 28 may also be inlaid in the blind holes opened on the curved face side 11, and the roll-grooves 32 are provided on the recessed portion 31. The balls 28 are locked into the roll-grooves 32 and roll along a track defined by the roll-groove 32, which can prevent the two from fleeing in the axial direction.

In the embodiment of this application, the first groove 71 opened on the rotation members 51 provides a flowing in passage for the acid fracturing fluid. In particular, the first grooves 71 on the rotation members 51 on the same side cooperate to form a first through hole 7, and an external pipeline is connected with the first through hole 7 to allow the acid fracturing fluid to enter into the gap 9 formed between the rock cores 100 to be tested through the hole.

In some embodiments of this application, a second groove 72 of a predefined length may be opened on the rock core 100 to be tested, and the second groove 72 is connected with the first groove 71. The second groove 72 that be set may be used to simulate a perforation, which enlarges the range of application of the embodiments of this application. In particular, there are two common methods to create fractures in the stratum: hydrofracturing and acidic etching the stratum rocks. Wherein, hydrofracturing is mainly used in creation of a fracture in softer reservoirs; when the reservoir manifests characteristics of high intensity and hardness of a carbonate reservoir, but hydrofracturing cannot destroy harder stratum rocks, then the acid fracturing fluid may be used to dissolve or melt the rocks with high intensity and hardness. Therefore, in practical projects, acid fracturing not only plays a role for acidic etching hard rocks, but also has the function of hydrofracturing. Thus, the second groove 72 set in this embodiment is used to simulate a perforation, after the acid fracturing fluid that entered into the second groove 72 has finished the acidic etching of the rock core 1, the acid fracturing fluid has a certain pressure and can play a support role on the flat face side of the rock core 1, and the support role has a similar effect as hydrofracturing.

Upon completion of the acidic etching of the rock core 100 to be tested by the acid fracturing fluid by means of the embodiments of this application, a test of flow conductivity is able to be performed to the pore canal formed by the etching, so as to evaluate the acidic etching capability of the acid fracturing fluid to the rock cores, and provide experimental references to practical constructions. The solution usually used in the test may be ammonia chloride ($NH_4Cl$) solution.

In an embodiment of this application, the two rock core holders 1 are sealed in an outer circumferential direction thereof, and when the flat face sides 13 of the two rock core holders 1 are spaced apart at a predefined distance, the gap 9 formed between the rock cores 100 to be tested is sealed. For simplification of the figures, the sealing apparatus for sealing the outer circumferential direction is omitted.

An embodiment of this application also provide a system for testing that applies the above mentioned performance testing device for acid fracturing fluid. Please refer to FIG. 6. The system comprises: a predefined number of the performance testing devices 10 for acid fracturing fluid, and a gripping device 20 for gripping the performance testing devices 10 for an acid fracturing fluid, and a second rotation axis 40 provided on the gripping device 20.

Figure 6:
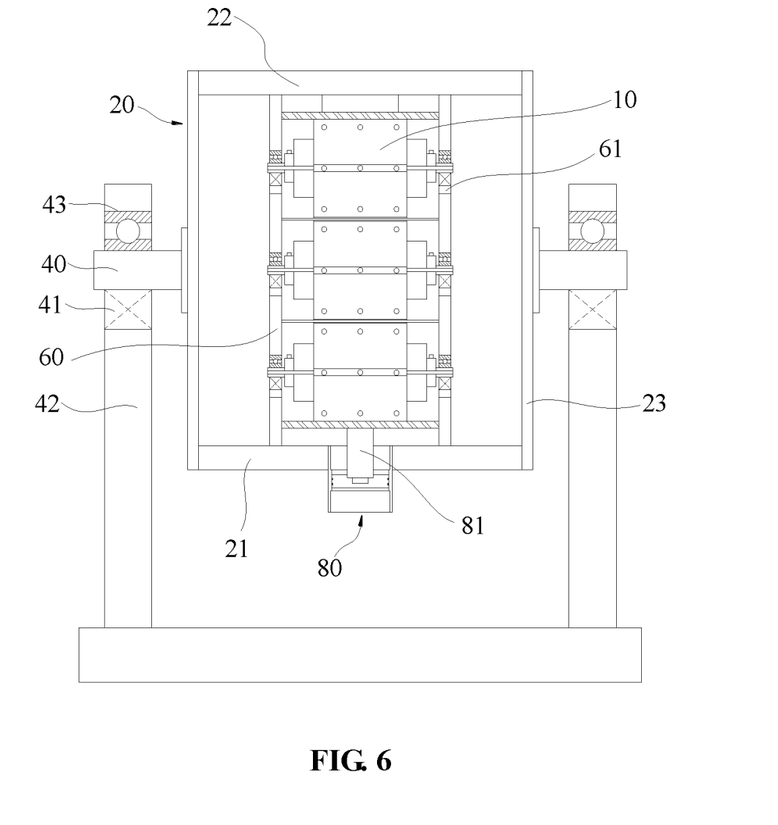
FIG. 6 is a structural diagram of the performance testing device for acid fracturing fluid of an embodiment of this application.

In this embodiment, the rock core of each performance testing device 10 for acid fracturing fluid can rotate about a first rotation axis 5, meanwhile, the gripping device 20 grips the predefined number of the performance testing devices 10 for acid fracturing fluid together whereafter they can rotate together about the second rotation axis 40, so that performance tests for multiple rock cores of different properties can be realized at a time, which greatly improves the testing frequency.

Figure 8:
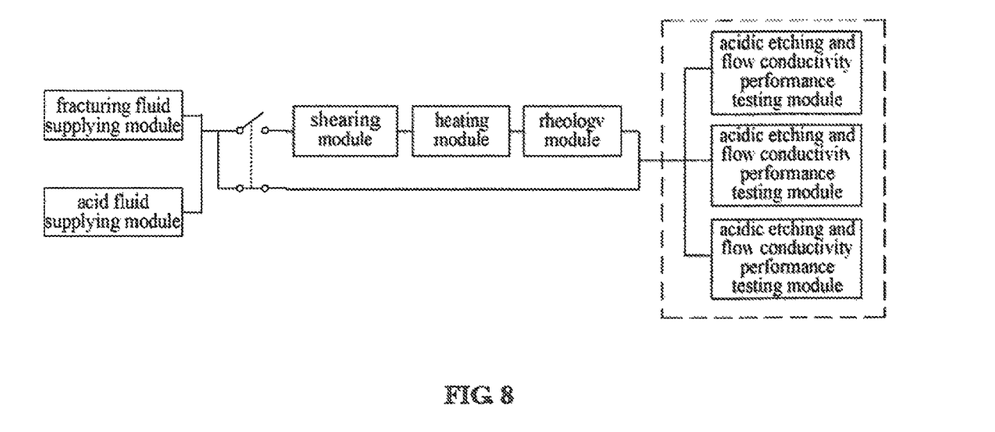
FIG. 8 is a module flow chart of an application example of the performance testing system for acid fracturing fluid of the embodiments of this application.
Figure 9:
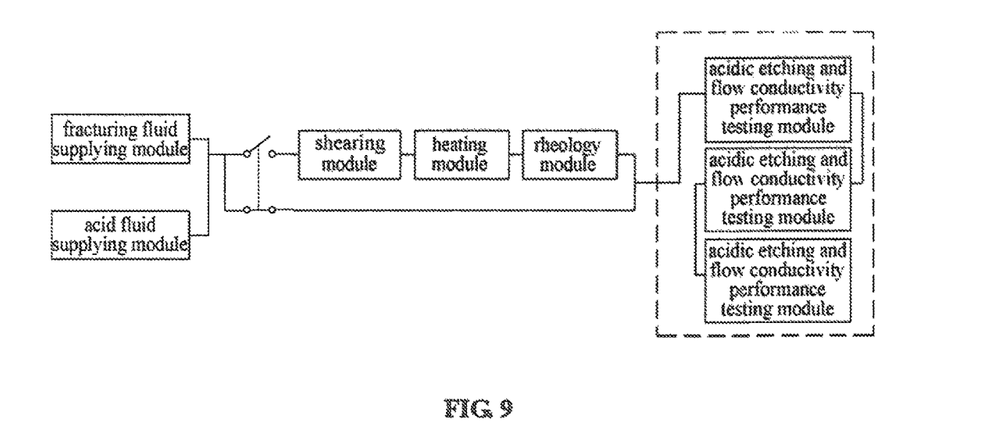
FIG. 9 is a module flow chart of another application example of the performance testing system for acid fracturing fluid of the embodiments of this application.

In addition, another advantageous effect of the combined use of the performance testing devices 10 for acid fracturing fluid in an embodiment of this application is that the predefined number of performance testing devices 10 for acid fracturing fluid is able to be connected in series or in parallel according to the experimental requirements, thereby increasing the degree of freedom of the experiment choices. In particular, please refer to FIGS. 8 and 9. Wherein, the acidic etching and flow conductivity performance testing modules shown in FIG. 8 are connected in parallel, and the acidic etching and flow conductivity testing modules shown in FIG. 9 are connected in series. The acidic etching and flow conductivity testing modules shown in the figures can employ the performance testing system for acid fracturing fluid of the embodiment of this application, and the number thereof is able to be selected freely according to the practical requirements. The rock cores used for the test may come from a same reservoir, for testing the acidic etching capability of the acid fracturing fluid to the rock cores located at different angles in the same reservoir; and the rock cores used for the test may also come from different reservoirs, for testing the acidic etching capability of the acid fracturing fluid to the rock cores located at the same or different angles in different reservoirs.

The shearing module shown in the figures is used to simulate the shearing effect caused by frictions between the acid fracturing fluid and the well casing wall when the acid fracturing fluid flows in the well casing before entering the stratum fractures. The rheology module is used to test a rheological performance and/or a friction performance of the acid fracturing fluid after shearing. Besides, in order to authentically reflect the temperature condition of the stratum, a heating module is provided before testing the rheological performance and/or the friction performance of the acid fracturing fluid, so as to heat the acid fracturing fluid. In addition, in order to realize self-sufficiency of the acid fracturing fluid, some embodiments of this invention may also comprise a fracturing fluid supplying module and an acid fluid supplying module. References can be made to an utility model of which the publication number is CN204177652U for the devices employed for the fracturing fluid supplying module, acid fluid supplying module, shearing module, heating module and rheology module shown in the figures. Since these devices are the prior art, no further description thereof will be given. As can be seen from the figures, the embodiments of this application may conduct the performance test for acid fracturing fluid separately, and may also perform the shearing, heating and flow conductivity performance tests for the acid fracturing fluid before conducting the performance test therefor, so as to authentically reflect the actual acid fracturing situation.

Please refer to FIG. 6. In some embodiments of this application, the gripping device 20 may comprise: a first support member 21 for placing the performance testing device 10 for acid fracturing fluid; a second support member 22 arranged opposite to the first support member 21; and a connecting member 23 that connects the first support member 21 and the second support member 22, the second rotation axis 40 being provided on the connecting member 23. The gripping device 20 is used to fix the performance testing device 10 for acid fracturing fluid to prevent it from displacing or fleeing during the experiment process.

In some embodiments of this application, a first support column 60 is provided between the first support member 21 and the second support member 22, the first support column 60 is opened with a predefined number of first axle holes 61, and the first axle hole 61 has a predefined length in a direction determined by pointing from the first support member 21 to the second support member 22; the first rotation axis 5 is able to be set in the first axle hole 61. To configure the first axle hole 61 to have a predefined length in the pressure applying direction is for reserving an appropriate leeway for mounting and rotating the rock core holder, and is also for preventing the first rotation axis 5 from being fixed by the first axial hole 61 which may cause frustration of the pressure applying purpose.

In order to apply pressure to the rock core to be tested through the pressure applying shell of the performance testing device 10 for acid fracturing fluid, some embodiments of this application also provide a pressure applying device. Please refer to FIG. 6. The pressure applying device comprises: a pressure applying device 80 provided on the first support member 21 and/or the second support member 22, the pressure applying device 80 has an extensible pressure output shaft 81, and the pressure output shaft 81 is able to be connected in a manner of abutting contact to the pressure applying shell 3 of the performance testing device 10 for acid fracturing fluid. The extension of the pressure output shaft 81 drives the pressure applying shell 3 to apply pressure to the rock core.

Figure 7:
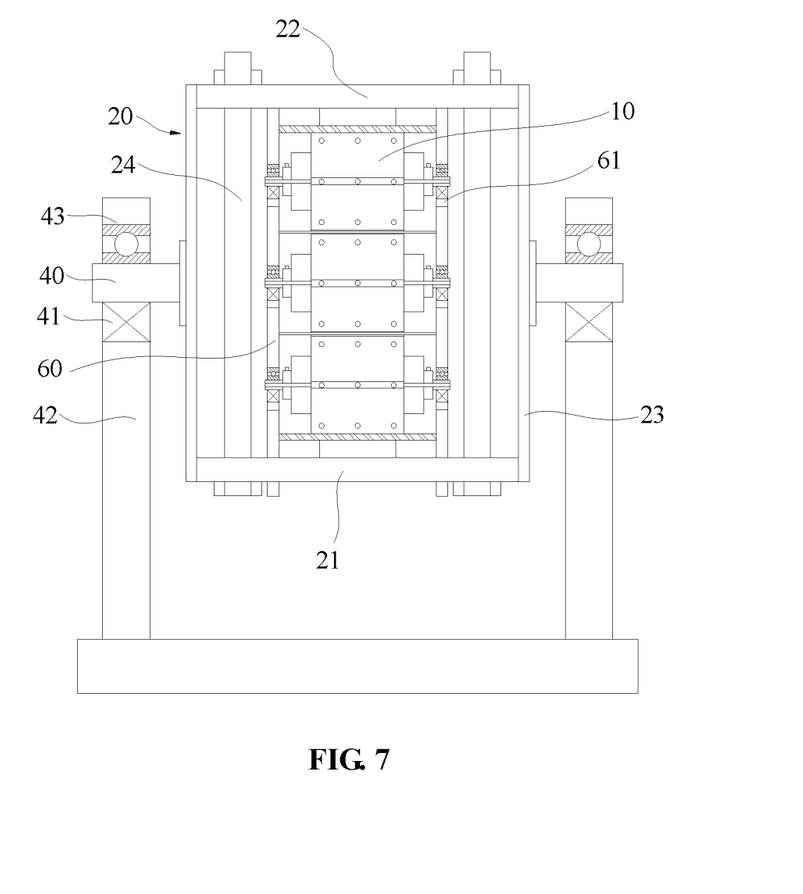
FIG. 7 is a structural diagram of the performance testing device for acid fracturing fluid of another embodiment of this application.

Please refer to FIG. 7. The embodiments of this application also provide a simple pressure applying device. That is, the first support member 21 and/or the second support member 22 is able to be movably connected to the connecting member 23, the movable direction is in accordance with the length of the first axle hole 61; for example, a track is provided in a lengthwise direction of the connecting member 23 for sliding of the first support member 21 and/or the second support member 22, such that the first support member 21 can come close to or be away from the second support member 22, or the two can come close to each other or be away from each other, i.e., the distance between the first support member 21 and the second support member 22 can be changed.

One of the first support member 21 and the second support member 22 is fixedly connected to an side of the first support column 60; correspondingly, the other one of the first support member 21 and the second support member 22 is opened with a second through hole (not shown in the figure) through which the other side of the first support column 60 can pass movably; as shown in FIG. 7, that is to open a second through hole on the first support member through which an side of the first support column 60 can pass movably, and the second support member 22 is securely connected to the other side of the first support column 60. Of course, in practice, a second through hole through which an side of the first support column 60 can pass movably may also be opened on the second support member 22, and the first support member 21 is securely connected to the other side of the first support column 60. A bolt 24 is connected between the first support member 21 and the second support member 22. The embodiments of this application drive the first support member 21 and/or the second support member 22 to move by means of the nut screwed on the bolt 24, thereby fastening or releasing the pressure applying shell 3 of the performance testing device 10 for acid fracturing fluid, which can also realize the pressure applying purpose.

In addition, for integrally fixation, some embodiments of this application also comprise a second support column 42, which is provided with a second axle hole 43, and the second rotation axis 40 is able to be set in the second axle hole 43. Besides, in order to reduce as far as possible the rigid rotation between the second rotation axis 40 and the second axle hole 43, a fixed bearing 41 may be fixed on the second rotation axis 40.

The above are only several embodiments of this invention, and a person skilled in the art can make various alternations or modifications to the embodiments of this invention according to the contents disclosed in the application document without deviating from the spirits and ranges of this invention.

The invention claimed is:

1. A performance testing device for acid fracturing fluid, comprising:
   two semiterete rock core holders having a curved face side, a flat face side and two opposite semicircle sides, the flat face side of the two semiterete rock core holders being arranged opposite to each other and being able to fix a rock core to be tested; the two semicircle sides of the two semiterete rock core holders being provided with a rotation member which is opened with a first groove; when the flat face sides of the two semiterete rock core holders being spaced apart at a predefined distance, the two rotation members being able to cooperate to form a first rotation axis, and the two first grooves being able to cooperate to form a first through hole; the two semiterete rock core holders being able to rotate about the first rotation axis, and the first through hole being able to be in communication with a gap formed between the rock cores fixed by the flat face sides of the two semiterete rock core holders;
   a pressure applying shell having a recessed portion that matches with the curved face side of the semiterete rock core holder, the recessed portion being able to rotatably cooperate with the curved face side, the pressure applying shell being able to apply a pressure to the two semiterete rock core holders to make the two flat face sides thereof joint in a manner of surface contact.

2. The device according to claim 1, wherein: the flat face side is opened with a slot in an axial direction of the semiterete rock core holder, the slot being able to lock the rock core to be tested.

3. The device according to claim 1, wherein: one of the recessed portion of the pressure applying shell and the curved face side of the semiterete rock core holder is provided with a predefined number of blind holes in which balls are inlaid.

4. The device according to claim 3, wherein:
   the predefined number of balls are divided into a predefined number of rows along an axial direction of the semiterete rock core holder to be inlaid in the blind holes;
   correspondingly, the other one of the recessed portion of the pressure applying shell and the curved face side of the rock core holder is provided with a predefined number of roll-grooves in a rotatable circumferential direction of the semiterete rock core holder, wherein each of the roll-grooves corresponds to the ball in the same row.

5. A system having the performance testing device for acid fracturing fluid according to claim 1, comprising:
   a predefined number of the performance testing devices for acid fracturing fluid;
   a gripping device for gripping the performance testing devices for acid fracturing fluid; and
   a second rotation axis provided on the gripping device.

6. The system according to claim 5, wherein, the gripping device comprises:
   a first support member for placing the performance testing devices for acid fracturing fluid;
   a second support member provided opposite to the first support member; and a connecting member that connects the first support member and the second support member, the second rotation axis being provided on the connecting member.

7. The system according to claim 6, wherein:
a first support column is provided between the first support member and the second support member, the first support column is opened with a predefined number of first axle holes, which have a predefined length in a direction determined by pointing from the first support member to the second support member;
the first rotation axis is able to be placed in the first axle hole.

8. The system according to claim 7, wherein: a pressure applying device is provided on the first support member and/or the second support member, the pressure applying device has an extendable pressure output shaft, and the pressure output shaft is able to be connected in a manner of abutting contact to the pressure applying shell.

9. The system according to claim 6, wherein:
the first support member and/or the second support member is able to be movably connected with the connecting member, and the movable direction is in accordance with a length direction of the first axle hole;
one of the first support member and the second support member is fixedly connected with an end of the first support column;
correspondingly, the other one of the first support member and the second support member is opened with a second through hole through which the other end of the first support column is able to pass movably;
a bolt is connected between the first support member and the second support member.

10. The system according to claim 5, further comprising:
a second support column on which a second axle hole is provided;
the second rotation axis is able to be set in the second axle hole.

11. A system having the performance testing device for acid fracturing fluid according to claim 2, comprising:
a predefined number of the performance testing devices for acid fracturing fluid;
a gripping device for gripping the performance testing devices for acid fracturing fluid; and
a second rotation axis provided on the gripping device.

12. A system having the performance testing device for acid fracturing fluid according to claim 3, comprising:
a predefined number of the performance testing devices for acid fracturing fluid;
a gripping device for gripping the performance testing devices for acid fracturing fluid; and
a second rotation axis provided on the gripping device.

13. A system having the performance testing device for acid fracturing fluid according to claim 4, comprising:
a predefined number of the performance testing devices for acid fracturing fluid;
a gripping device for gripping the performance testing devices for acid fracturing fluid; and
a second rotation axis provided on the gripping device.

* * * * *